(12) United States Patent
Abitbol et al.

(10) Patent No.: US 6,663,894 B2
(45) Date of Patent: Dec. 16, 2003

(54) INTRAOCULAR TRANSPLANTATION OF ENCAPSULATED CELLS

(75) Inventors: Marc Abitbol, Paris (FR); Yves Uteza, Villejuif (FR); Maurice Menasche, Villiers-Le-Bel (FR); Carine Bossard, Toulouse (FR); Loic Van Den Berghe, Paris (FR); Sebastian Bonnel, Paris (FR); Hervé Prats, Toulouse (FR); Jiri Honiger, Vitlejuif (FR); Martin Neuner-Jehle, Gif-Sur-Yvette (FR)

(73) Assignees: Universite de Paris V Rene-Descartes, Paris (FR); Association Francaise Retinitis Pigmentosa, Cedex (FR)

(*) Notice: Subject to any disclaimer, the term of this patent is extended or adjusted under 35 U.S.C. 154(b) by 0 days.

(21) Appl. No.: 09/775,174

(22) Filed: Feb. 1, 2001

(65) Prior Publication Data

US 2002/0076396 A1 Jun. 20, 2002

Related U.S. Application Data

(62) Division of application No. 09/449,293, filed on Nov. 24, 1999, now Pat. No. 6,267,954.

(51) Int. Cl.[7] .......................... A61K 9/14; A61K 38/00; A01N 63/00; C12N 5/00; C12N 5/06
(52) U.S. Cl. ...................... 424/489; 424/93.7; 435/325; 435/352; 435/360; 514/12
(58) Field of Search .................. 424/93.7, 489, 424/93.3, 93.1; 435/325, 172.3, 347, 382

(56) References Cited

U.S. PATENT DOCUMENTS

| | | | |
|---|---|---|---|
| 5,374,616 A | * | 12/1994 | Spiegel et al. .................. 514/4 |
| 5,656,481 A | | 8/1997 | Baetge et al. |
| 5,859,208 A | | 1/1999 | Fiddes et al. |

OTHER PUBLICATIONS

Serguera et al. :Control of Erythropoietin Secretion by Doxycycline or Mifepristone in Mice Bearing Polymer–Encapsulated Engineered Cells; Human Gene Therapy, Feb. 1999 10:375–383.*

Uteza et al., "Intravitreous transplantation of encapsulated fibroblasts secreting the human fibroblast growth factor 2 delays photoreceptor cell degeneration in Royal College of Surgeons rates", *Proc. Natl. Acad. Sci. USA,* vol. 96, pp. 3126–3131 (Mar. 1999).

* cited by examiner

*Primary Examiner*—Jon P. Weber
*Assistant Examiner*—Patricia A Patten
(74) *Attorney, Agent, or Firm*—Merchant & Gould P.C.

(57) ABSTRACT

Compositions and methods for reducing ocular diseases by implanting in an eye of a subject a composition comprising encapsulated cells which produce polypeptides, more particularly polypeptides that exhibit neurotrophic and/or anti-angiogenic activity. The encapsulation prevents the entry of host immune cells in the microcapsule while permitting the release of the polypeptide outside of the microcapsule.

8 Claims, 12 Drawing Sheets

FIG. 7
1.
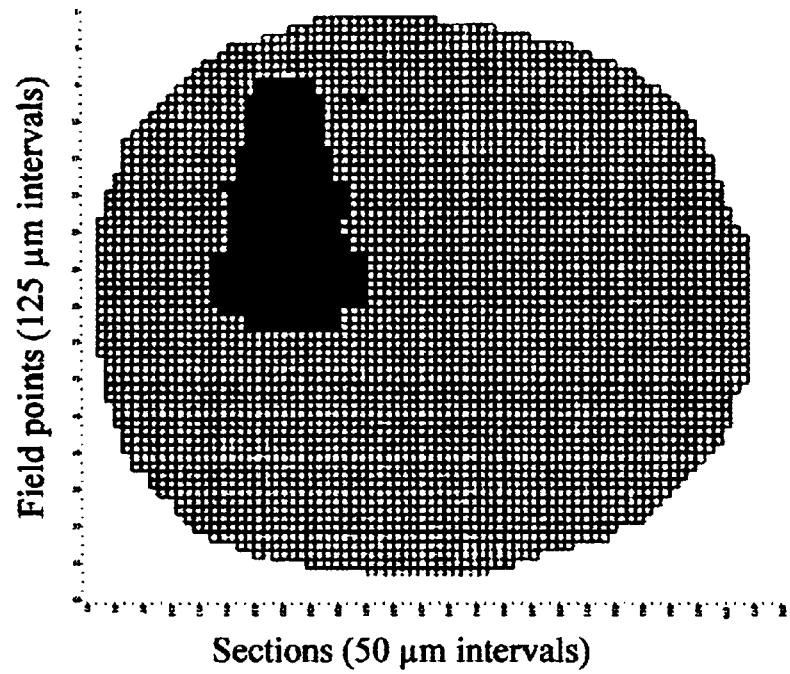
2.
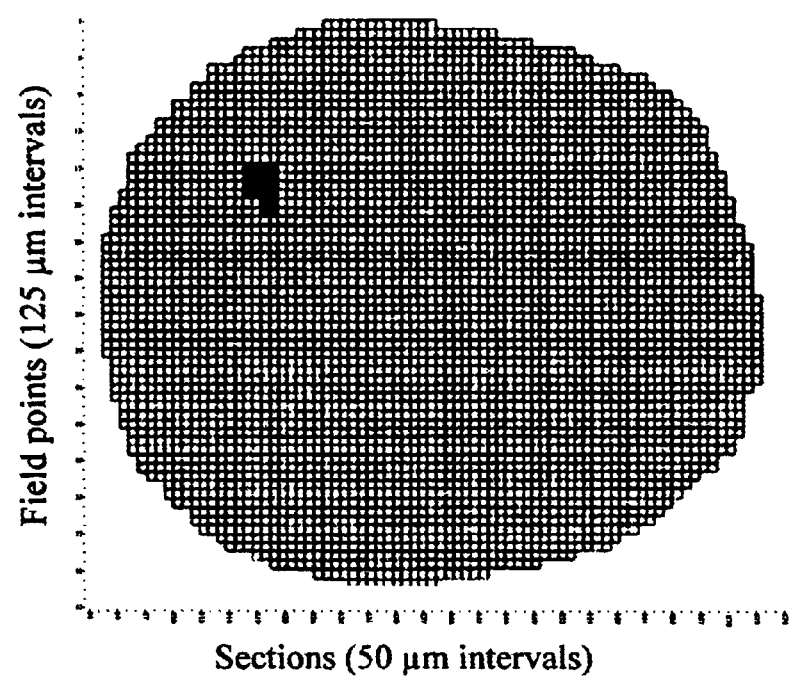

FIG. 11 signal peptide
CCCGGGCCTTCGGGCCGGGGAGGAAGAGTAGCTCGCCGAGGCCGAGGAGAGCGGGC
CGCCCCACAGCCGAGCCG
GAGAGGAGGCGAGCGGCGCGCCCGTCGGGCTCCGAAACCATGAACTTTCTG
CTGTCTTGGGTGCATTGG
AGCCCTTGCCTTGCTCTACCTCCACCATGCCAAGTGGTCCCAGGCTGCACCC HA tag
ATGACTTACCCATACGATGTTCCAGATTACGCTAGCTTGGGTGGTCATATGGCCATGG
AGGCCCCGGGGATCCGAATTC endostatine
GCTCATACTCATCAGGACTTTCAGCCAGTGCTCCACTGGCTGAACACCCCC
TGTCTGGAGGCATGGCTG
GTATCCGTGGAGGCAGATTTCCAGTGCTTCCAGCAAGCCCGAGCCGTGGGGCTGTGCGGG
CACCCTTCCGGGCTTTCCT
GTCCTCTAGGCTGCAGGATCTCTATAGCATCGTGCGCCGTGCTGACCGGGGTCTGTG
CCCATCGTCAACCTGAAG
GACGAGGTGCTATCTCCCAGCTGGGACTCCCTGTTTCTGGCTCCCAGGGTCAACTGC
AACCCGGGCCCGCATCT
TTTCTTTTGACGGCAGAGATGTCCTGAGACACCCAGCCTGGCCGCAGAAGAGCGTAT
GGCACGGCTCGACCCCAG
TGGGCGGAGGCTGATGGAGAGTTACTGTGAGACATGGCAACTGAAACTACTGGGGC
TACAGGTCAGGCCTCTCC
CTGCTGTCAGGCAGGCTCCTGAACAGAAAGCTGCGAGCTGCCACAACAGCTACATC
GTCCTGTGCATTGAGAATA
GCTTCATGACCCTTCTTTCTCCAAATAG

INTRAOCULAR TRANSPLANTATION OF ENCAPSULATED CELLS

This application is a divisional of application Ser. No. 09/449,293 now U.S. Pat. No. 6,267,554, filed Nov. 24, 1999, which application(s) are incorporated herein by reference.

FIELD OF THE INVENTION

The present invention relates to compositions and methods for the delivery of biologically active molecules to the eye. The invention relates more particularly to encapsulated cells, their preparation and use to deliver in vivo effective amounts of biologically active molecules. The invention is particularly suited for the treatment of photoreceptor degeneration retinopathies or cancers.

BACKGROUND AND PRIOR ART

There are many diseases of the eyes or ocular diseases which affect vision. Some of these diseases include diseases of the conjunctiva and cornea which can produce loss of visual acuity, pain and discharge, cataracts resulting in blurred vision, glare altered color perception and monocular diplopia, uveal diseases resulting in photophobia, ocular discomfort and visual blurring, retinal diseases resulting in distortion of straight lines (metamorphopsia), loss of central acuity and visual field abnormalities and diseases of Bruch's membrane, which may lead to age-related macular degeneration.

Among numerous forms of human retinopathies, age-related macular degeneration (hereinafter referred to as AMD) is the leading cause of severe vision loss in the elderly and affects between 6.4% (New Zealand) (19) and 6.9–11.4% (U.S.A.) (20, 21) of people beyond the age of 65. AMD is a heterogeneous group of retinal degenerations which is associated with alterations of retinal pigment epithelium (RPE) cells.

In the past transplantation of rod-enriched adult photoreceptor cell populations that may protect the macula from secondary degeneration in rod-cone retinitis pigmentosa affected patients was generally the therapy of choice for retinal degenerations, including AMD. However, the photoreceptors that were to be transplanted usually came from adult or embryonic human photoreceptors collected postmortem. These photoreceptors can thus be infected by a diversity of viruses including the hepatitis virus, cytomegalovirus, and human immunodeficiency virus as well as other pathogens such as prions that may remain undetectable prior to transplantation. Additionally, these cells may trigger a strong immune response in the host, leading to the destruction of the graft and/or to inflammatory autoimmune reactions.

Moreover, oculo gene therapy protocols which relied on the basis of cell transfection, viral cell infection, or cell transplantation were also known in this art. However one problem with the known gene therapy protocols was that adverse immunological side effects occurred. These adverse side effects, in some instances, could lead to anaphylactic shock, endangering the patient.

Among various protocols which have been designed to transfer therapeutically important genes to a target tissue, the transplantation of genetically engineered cells has become particularly promising in recent years. To protect allogeneic or xenogeneic grafts from immune rejection, cells have been successfully microencapsulated with non-degradable biocompatible polymers and used for the experimental treatment of several disorders such as type I diabetes mellitus (1–5), dwarfism (6), hemophilia B (7), anemia (8), chronic pain (9, 10), amyotrophic lateral sclerosis (11), as well as Parkinson's, Huntington's, and Alzheimer's diseases (12–18). However, none of these cited references taught a method for treating ocular diseases.

Thus, it is an object of the present invention to provide genetically modified cells which stably produce therapeutic factors suitable for treating ocular disorders.

It is another object of the present invention to provide methods of encapsulating such genetically modified cells, in such a way that the cells remain viable and produce effective amounts of the biologically active agent(s) in the eye, more particularly in the retina.

It is another object of the present invention to provide a method for implanting in vivo these devices (encapsulated cells), and the effective release and treatment of ocular disorders in vivo.

It is another object of the present invention to provide ocular compositions that can be surgically retrieved from the ocular globes, for instance, in case of an occurrence of adverse side effects.

It is yet another object of the present invention to provide compositions and methods to deliver biologically active molecules to the eye to treat ocular disorders that are bacteriological and virological safe.

It is yet another object of the present invention to provide genetically engineered cell lines that can be systematically tested for any kind of pathogens before they are encapsulated and transplanted into human eyes.

It is yet another object of the present invention to provide a therapeutic method to promote the survival of photoreceptor cells in degenerating retinas of mammals in order to treat retinal degenerations, as well as treating mammals that have retinitis pigmentosa or age-related macular degeneration.

These and other objects are achieved by the present invention as evidenced by the summary of the invention, description of the preferred embodiments and the claims.

SUMMARY OF THE INVENTION

In one of the method aspects, the present invention provides a method for delivering a polypeptide to an ocular cell of a subject in vivo said method comprising the step of:

(a) implanting in an eye of said subject a composition comprising cells which produce said polypeptide wherein said cells are encapsulated.

In another method aspect, the present invention provides a method for reducing an ocular disease comprising the step of:

(a) administering to a subject in need of said treatment a composition comprising encapsulated cells wherein said cells produce a biologically active polypeptide for reducing said ocular disease.

In a composition aspect, the present invention provides a composition comprising encapsulated cells which produce an endostatin or a fibroblast growth factor polypeptide.

Figure 2:
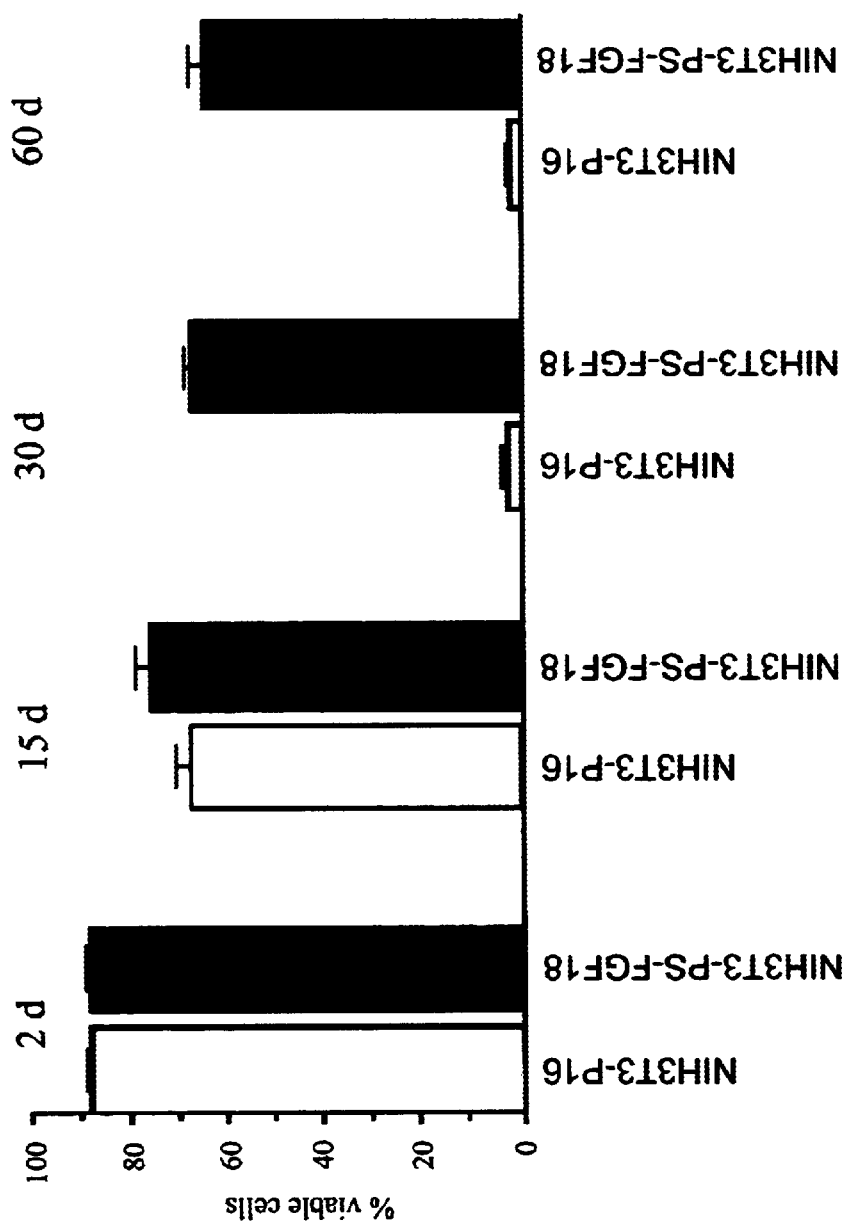

FIG. 2. is a graphic representation of the survival rate of NIH3T3-P16 and NIH3T3 PS-FGF18 cells in 4.0 mm microcapsules, as measured at 2, 15, 30, and 60 days post-encapsulation. Viable cells were identified by trypan blue exclusion assays and are indicated as the mean percentage of the total number of encapsulated cells. Bars: s.e.m. (n=6).

Figure 3:
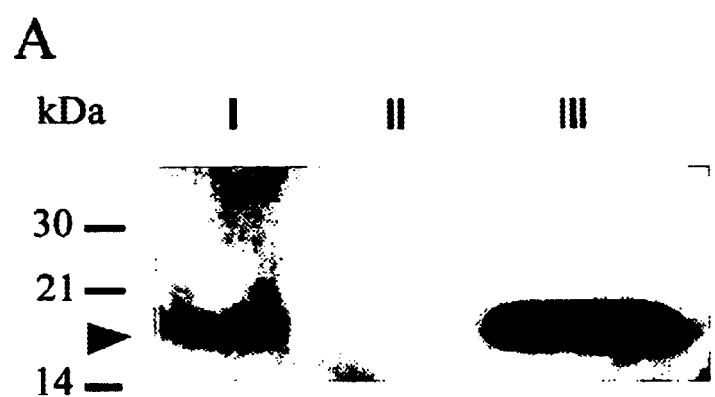

FIG. 3. is a Western blot of crude cell extracts (105 cells/lane) revealing the 18 kDa hFGF-2 protein in NIH3T3 PS-FGF18 cells (lane I, arrow head). Lane II is an NIH3T3-P16 cell extract. Lane III is recombinant hFGF-2 (10 ng).

Figure 4:
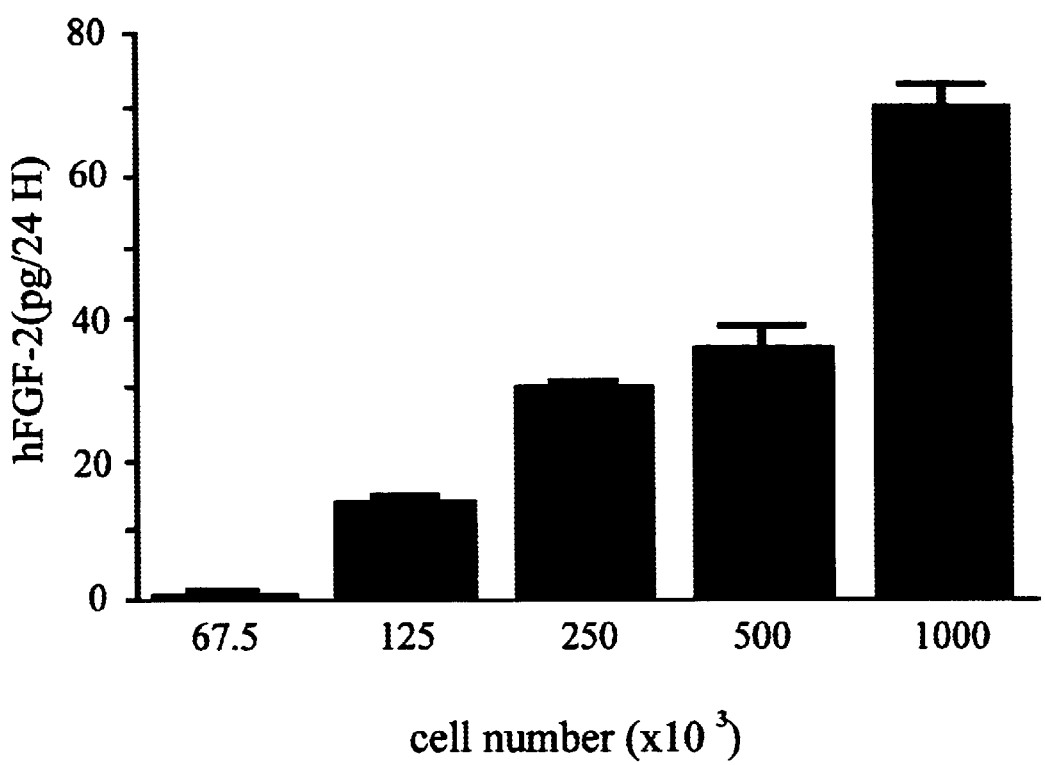

FIG. 4 is a graphical representation of the secretion of hFGF-2 protein by NIH3T3 PS-FGF18 cells at different concentrations. Data are expressed as mean values (pg/24 h)±s.e.m. (n=6).

Figure 5:
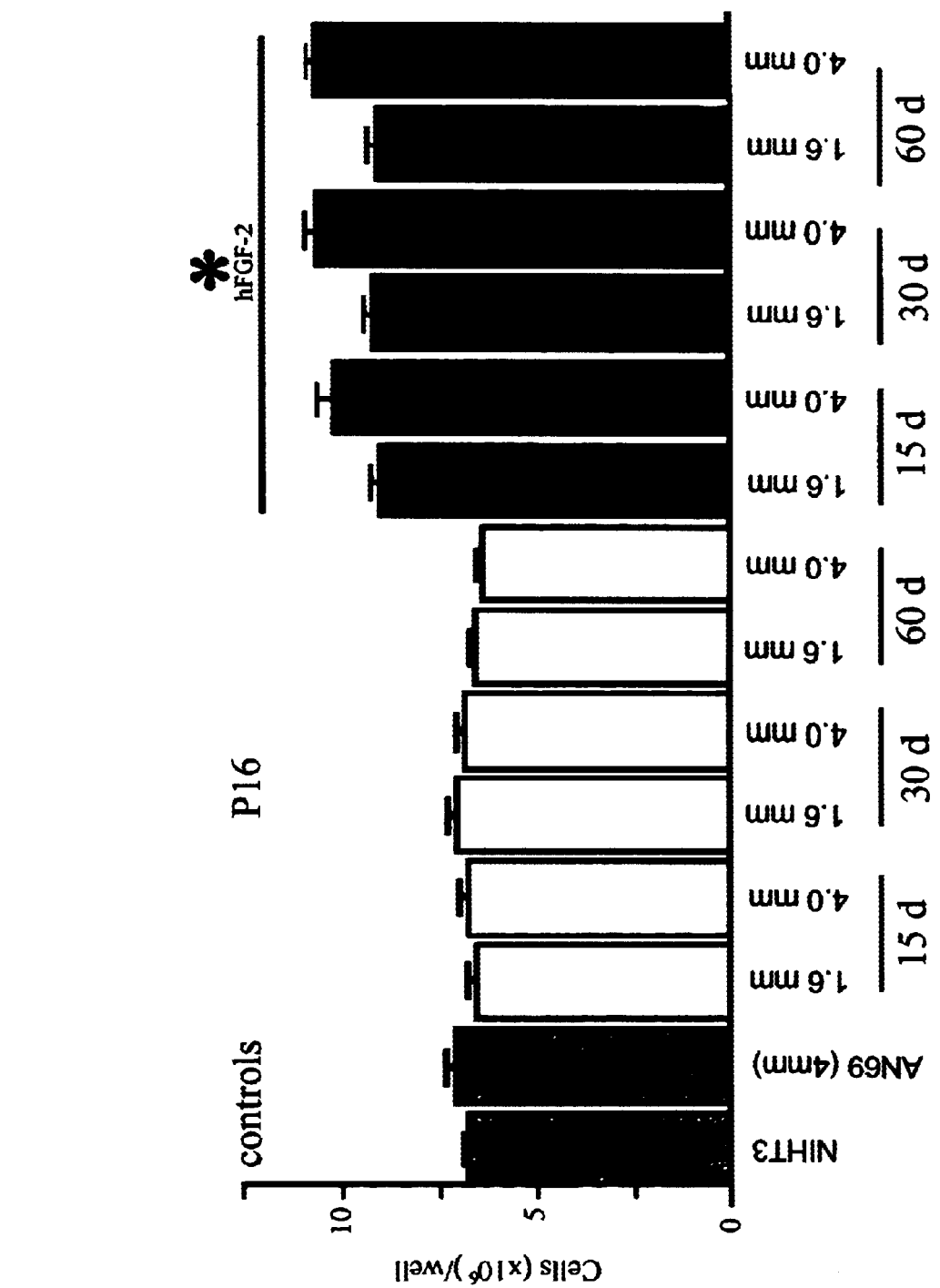

FIG. 5 is a graphical representation of a bioassay of hFGF-2 secretion from 1.6 mm and 4.0 mm capsules filled with either NIH3T3-P16 or NIH3T3 PS-FGF18 cells and kept in culture for 15, 30, or 60 days. Data are expressed as mean values±s.e.m. Statistics: Mann-Whitney U-test (*P= 0.001, n=6).

Figure 6:
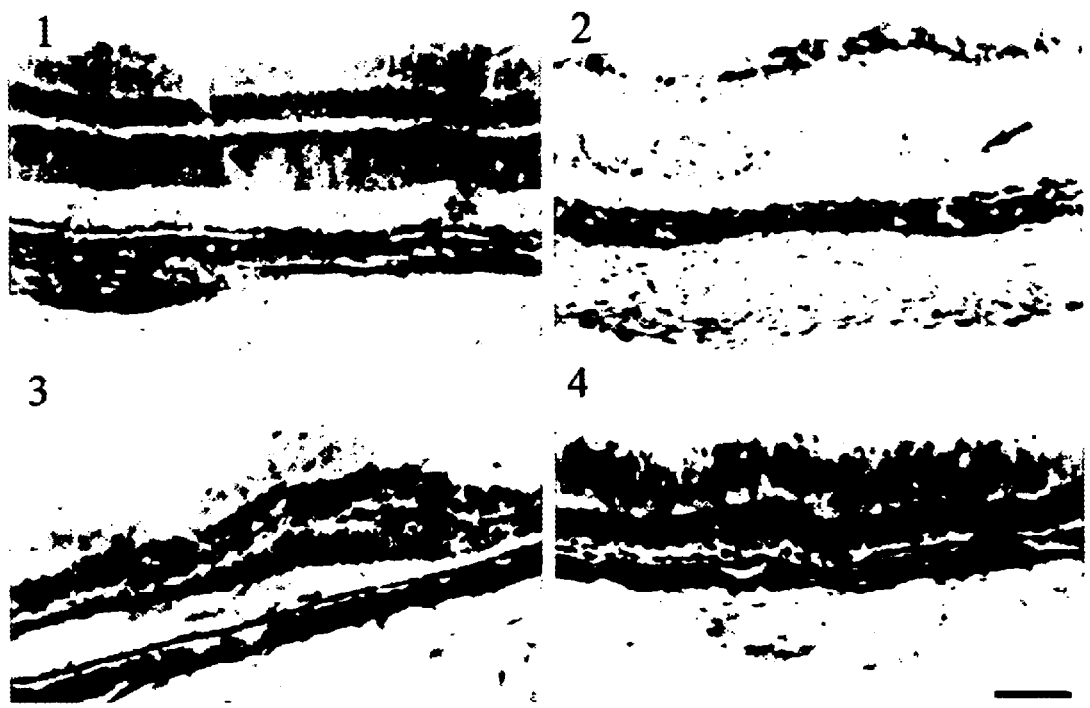

FIG. 6 are photographs of stained retinal tissues showing the retina of a 21-day-old rat before the beginning of photoreceptor cell degeneration (1). A dystrophic retina of a 63 day-old control rat eye (2). Photoreceptor cell rescue in a rat eye which received microencapsulated NIH3T3 PS-FGF18 cells and cut at 90 days post-transplantation (3). Note the microcapsule-proximal retina which comprises 5 to 6 photoreceptor cell layers (arrow). The retina of an ocular globe proximal to a NIH3T3P16 cell-filled microcapsule, cut at 90 days post-transplantation (4). The photoreceptor cell layer is indicated by arrows. Sections: 16 mm, toluidine blue staining. Scale bar: 20 mm.

FIG. 7 is a two-dimensional reconstruction of the retinal surface of treated RCS p+ rats showing maximal rescue effects. The retinal area with at least 5 photoreceptor cell layers is indicated in black. The region (4.10 mm$^2$) of delayed photoreceptor cell degeneration in the retina exposed for 45 days to a NIH3T3 PS-FGF18 cell-filled microcapsules indicated in (1). The area (0.15 mm$^2$) of delayed cell degeneration proximal to a NIH3T3-P16 cell-filled microcapsule as seen in the only eye which revealed a cell rescue effect at 90 days post-transplantation is indicated in (2).

Figure 8:

FIG. 8 is a photograph of a photoreceptor rosette formation in a RCS rat retina at 45 days post-transplantation. The microcapsule containing NIH3T3-P16 fibroblasts (asterisk) caused a cellular reorganization of the retina which led to the appearance of a photoreceptor rosette structure (arrow). The section (16 mm) was stained with toluidine blue. Scale bar: 40 mm.

Figure 9:
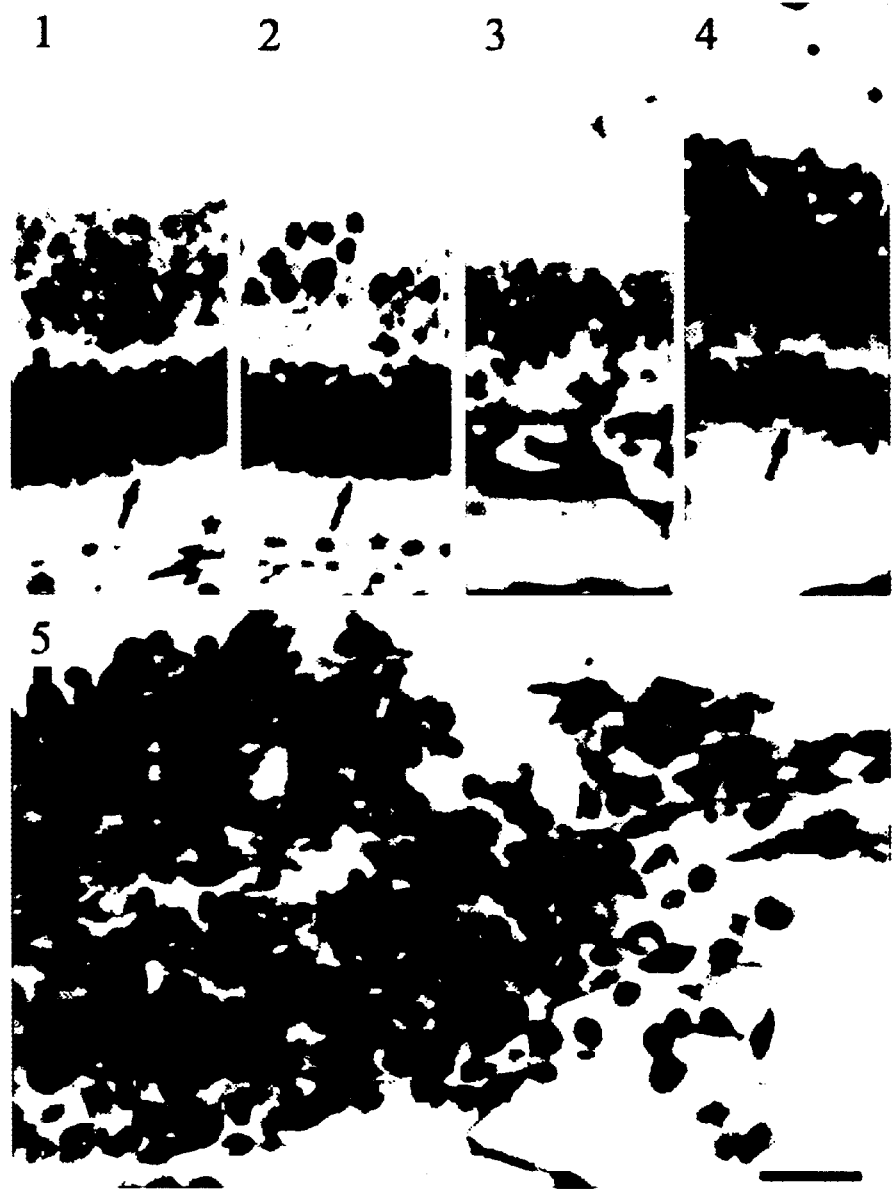

FIG. 9 are photographs of tissue sections of rat retinas. Photoreceptors are indicated by the arrows and retinal-pigment epithelial cells are represented by the asterisks. Normal 3-month-old RCS rdy+ albino are indicated in (1) and (2) and dystrophic 111-day-old RCS rat retina are indicated in (3) and (4). DAB-immunostaining without primary antibody (1; control) and with anti-FGF-2 antibodies (2–4). Note the lack of immunostaining in photoreceptor cells in the rescued retina (4). Cytoplasmic FGF-2 immunostaining in encapsulated NIH3T3 PS-FGF18 fibroblasts at 90 days post-transplantation is represented in (5). Antibody concentration: 10 ng/ml; parafin sections countercolorated with hematoxyline: 5 mm. Scale bar: 10 mm.

Figure 10:
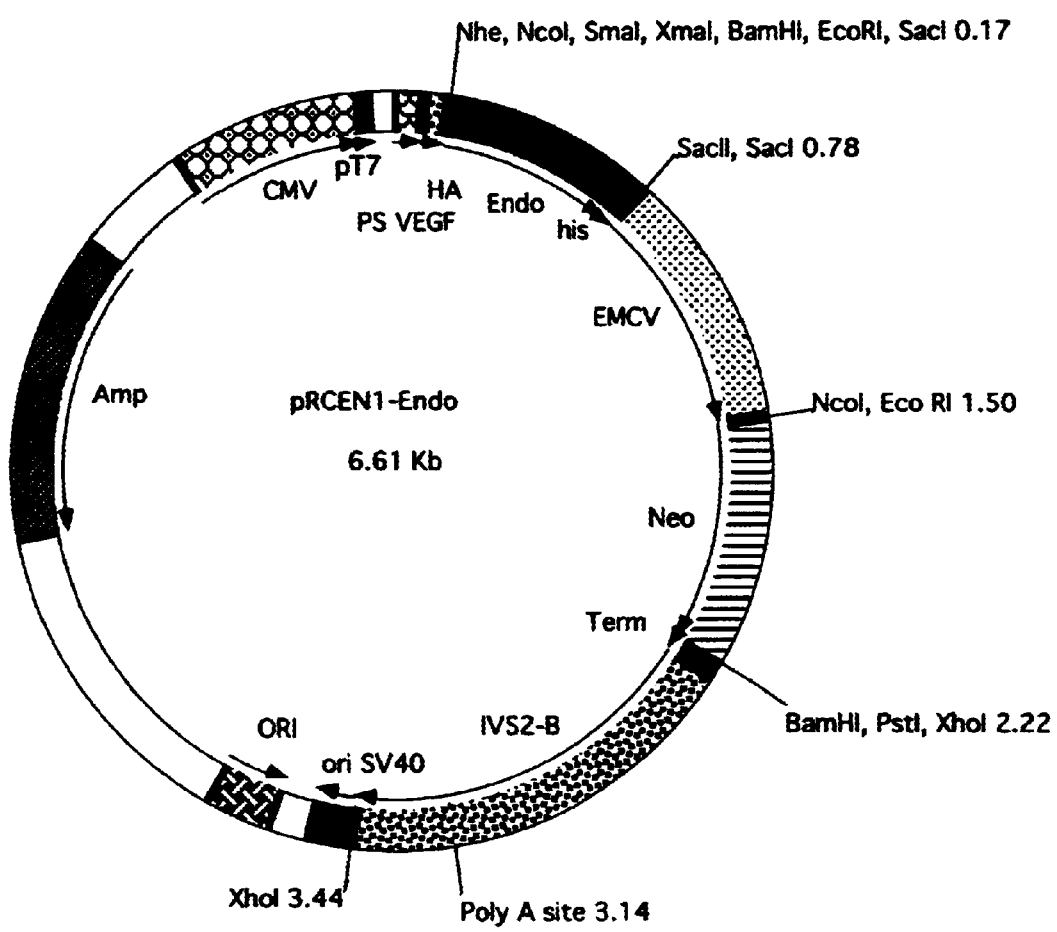

FIG. 10 is a graphical representation of plasmid pRCEN1-Endo.

FIG. 11 are nucleotide sequences of the peptide signal VEGF (SEQ ID NO:1), hemaglutinine (SEQ ID NO:2) and endostatin used to construct the plasmid pRCEN1-Endo (SEQ ID NO:3).

Figure 12:
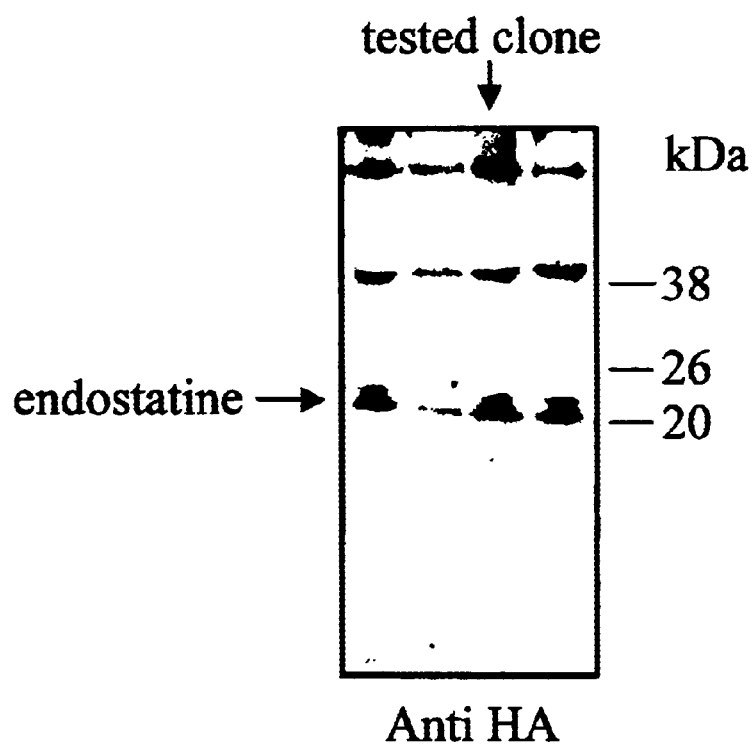

FIG. 12 is a Western blot of CHO cells transfected with pRCEN1-endo after TCA precipitation.

DETAILED DESCRIPTION OF THE PREFERRED EMBODIMENTS OF THE PRESENT INVENTION

As used herein the term "subject" refers to man or any animal that has eyes.

As used herein "biologically active", when referring to the polypeptide means that the polypeptide is capable of functioning.

As used herein "ocular disease" refers to a disease of the eye, including, but not limited to tumors, ocular degeneration, retinopathies, retinitis, retinal vasculopathies, diabetic retinopathies, diseases of the Bruch's membrane and the like.

As used herein, the term "reducing" also encompasses treating and alleviating the ocular disease.

More specifically, the present invention entails a method of delivering a polypeptide to an ocular cell in vivo comprising implanting, in the eye of a subject, a composition comprising cells which produce said polypeptide wherein said cells are encapsulated.

The invention also entails the use of encapsulated cells for the delivery of polypeptides in the ocular and more particularly the retina.

The instant invention can be used to deliver various polypeptides in the eye. In the context of this invention, the term "polypeptide" designates any protein or fragment thereof, peptide or any molecule composed of an amino acid sequence, preferably having biological activity. Preferred biologically active polypeptides according to the instant invention exhibit neurotrophic and/or anti-angiogenic activity. Typical examples of such polypeptides are ciliary neurotrophic factor (CNTF), glial-derived neurotrophic factor (GDNF), nerve growth factor (NGF), brain-derived neurotrophic factor (BDNF), NT3, nurturin, fibroblast growth factors (FGFs), endostatin, ATF, fragments of thrombospondin, variants thereof and the like. More preferred polypeptides are FGFs, such as acidic FGF (aFGF), basic FGF (bFGF), FGF-1 and FGF-2 and endostatin.

For use in mammalian subjects, it is preferred to use allogenic polypeptides. In particular, for use in human subjects, it is preferred to use encapsulated cells which produce a polypeptide of human origin. Obviously, it is also possible to deliver xenogenic polypeptides or variants thereof. In a specific example, the polypeptide is human FGF-2 or human endostatin or variants thereof. The term "variant" means any polypeptide having one or several structural modification(s) introduced therein, such as mutation(s), deletion(s), substitution(s) and/or addition(s) of one or several amino acid residues, the variant still exhibiting biological activity. The use of the instant invention to deliver any such variants can be performed by the skilled artisan following the teaching of the instant invention.

The compositions and methods of this invention use cells which produce the polypeptide. The cells can be primary cells or cell lines, in particular genetically modified primary cells or cell lines which produce the polypeptide. Preferably, the cells are eucaryotic cells, more preferably mammalian cells. The use of mammalian cells is advantageous since mammalian cells can produce polypeptides with appropriate post-translational modifications (glycosylations, maturation, etc.). The cells are preferably compatible with biological use in vivo and, in particular, do not exhibit known pathogenic activity. Examples of such cells include, but are not limited to, fibroblasts, muscle cells, hepatocytes, neural cells and the like, CHO cells, kidney cells, PC12 cell lines, MDCK cells, astrocytes, and the like.

It is particularly preferred to use cells which can proliferate, at least under certain culture conditions, in order to produce larger amounts of the polypeptide(s). Furthermore, the cells can be autologous (from the same subject), allogeneic (from a different subject of the same species) or xenogenic (from a different species). Indeed, since the cells are encapsulated prior to their administration, they are protected from the immune system of the receiving subject and can survive for long periods of time.

Specific examples of cells to be used in the instant invention include fibroblasts, such as murine fibroblasts, in particular NIH-3T3 cells; C2 cells, C12 cells, CHO cells, PC12 cells, and the like. In a preferred embodiment of this invention, fibroblast cells are used, in particular fibroblast cell lines.

At least some of the cells used in this invention produce a polypeptide to be delivered in the eye. Generally, the cells are genetically modified cells, i.e., they contain a recombinant nucleic acid molecule encoding the polypeptide. The nucleic acid construct encoding the polypeptide can be a DNA construct, in particular a cDNA or synthetic DNA and can be further modified to improve transcription/translation in a host cell. The nucleic acid can also be a RNA, for instance, a retroviral genome.

Preferably, the nucleic acid construct comprises, operably linked, a promoter region, a sequence encoding the polypeptide, and optionally, a termination signal. Even more preferably, the nucleic acid construct comprises a secretion signal, between the promoter and coding regions, which allows, or facilitates, the secretion of the polypeptide outside of the cells. The secretion signal may be homologous with respect to the polypeptide (i.e., from the same gene) or heterologous thereto (i.e., from any other gene encoding a secreted polypeptide, in particular a mammalian gene, or artificial). Examples of secretion signals include the signal peptide of vascular endothelial growth factor (VEGF), pre pro Nerve Growth Sequence (NGS) and the like.

The promoter region can be chosen from among all promoter regions that are functional in mammalian cells, in particular human cells. The promoter can be a strong or a weak promoter, a constitutive or a regulated/inducible promoter, an ubiquitous or selective promoter. The promoter can be of different origin such as cellular, viral, artificial and the like. Particular types of promoters are house-keeping promoters, i.e., promoters from cellular genes expressed in mammalian (e.g., human) tissues or cells, or viral promoters (CMV, LTR, SV40, etc.) Furthermore, the promoter region can be modified artificially to include enhancer element(s), inducibility element(s) and the like. The promoter, secretion signal and termination region sequences can be selected and adapted by the skilled artisan based on the polypeptide, the pathology, the vector used, etc. In this regard, the nucleic acid construct can be inserted in any various kinds of vectors such as plasmids, viruses, episomes, phages, artificial chromosomes and the like.

The cell composition can be prepared by contacting a cell culture with a nucleic acid construct, as defined above, encoding the polypeptide. The cells are then recovered and a selection step can be performed in order to isolate the cells which effectively contain the recombinant nucleic acid construct and express the polypeptide. The contacting can be made according to various methods known in the art and include electroporation, precipitation, gene gun, viral transduction, non-viral vector mediated transfection and the like. Preferably, the cells are contacted with the nucleic acid construct without a viral vector. In this regard, the nucleic acid construct can be inserted in a non-viral vector (a plasmid, cosmid, and the like) and contacted with the cell population either alone ("naked") or in the presence of a transfecting agent (liposome, polymer, cationic lipid and the like). The cells are then cultured according to known methods in order to provide sufficient amounts of transfected cells (usually above $10^4$ cells, preferably above $10^5$ cells). The cells can be used directly or stored for later use.

In a preferred embodiment, stable cell lines producing the polypeptide are prepared. These cells usually contain one or several copies of the nucleic acid construct incorporated into their genome, so that the progeny, daughter and/or derivatives of said cells still contain the nucleic acid construct and produce the polypeptide. The preparation of such cells is advantageous since they can be used in many different subjects where the polypeptide is to be produced. These cell lines can therefore be produced, cell banks can be made under appropriate quality conditions and stored.

In a preferred embodiment of this invention, a composition is used comprising mammalian cells containing a recombinant nucleic acid construct, said cells producing the polypeptide. Particularly preferred embodiments of this invention use a composition comprising mammalian cells containing (i) a recombinant nucleic acid construct encoding an endostatin polypeptide, said cells producing the endostatin polypeptide or (ii) a recombinant nucleic acid construct encoding a fibroblast growth factor, said cells producing the fibroblast growth factor. In a more preferred embodiment, the composition comprises genetically modified fibroblast cells producing the polypeptide.

As indicated, above, the methods and compositions of this invention use encapsulated cells. The term "encapsulated" means that the cells are contained in a biocompatible device or jacket which immunoisolates the cells. The cells are therefore preferably encapsulated in a biocompatible jacket which protects the encapsulated cells from the immune cells and allows the release of the polypeptide outside of the microcapsule. The main characteristics of the biocompatible material used for encapsulation should therefore be as follows:

(i) it does not significantly activate the complement system;

(ii) it allows the release of the polypeptide outside of the microcapsule; and (iii) it significantly prevents the entry of the host immune cells in the microcapsule.

Preferably, the biocompatible material used is a permeable or semi-permeable material with pores having an internal diameter below 400 µm, more preferably below 300 µm. Various biocompatible artificial polymers (or copolymers) can be employed for encapsulation, derived from cellulose, dextran, polyamide, polyurethane, acrylonitril, nylon, alginate-poly-L-lysine, hydroxyethyl methacrylate (HEMA), hydroxyethyl methacrylate-methyl methacrylate (HEMA-MMA), agarose-polystyrene alginate, etc. (2, 5, 6, 10–12, 14, 15, 17, 18, 34–42). In a specific embodiment, the copolymer AN69 (polyacrylonitril-methallylsulfonate) is used. The results presented in the examples show that this biopolymer provides efficient protection of encapsulated cells against the host immune system and long-term maintenance of cell viability. AN69 can be used as a semipermeable hemodialysis membrane and fails to activate the complement system. Other biocompatible materials include hydrogels and thermoplastic materials, as described in, for instance, U.S. Pat. No. 5,874,099, incorporated herein by reference.

The microcapsule or "jacket" can exhibit different forms. In particular embodiments of this invention, the microcapsule is shaped to form a fiber (in particular, a hollow fiber) or a sheet (in particular a flat or curved sheet). The size of the microcapsule which is usually below 1.0 cm long or its diameter can be adapted by the skilled artisan.

Preferably, the composition comprises at least $10^4$ encapsulated cells, more preferably at least $10^5$ cells. The number of encapsulated cells can be adapted by the skilled artisan depending on the cell type, the polypeptide, the size of the microcapsule, etc. For encapsidation the cells are deposited on the biomaterial in any appropriate medium. The cells, mounted by capillarity thus adhere to the biopolymer and can proliferate inside the microcapsules under culture and in oculo conditions, thus growing to confluence.

The composition can be implanted in different sites of the eye, preferably in the vitreous body of the eye, for instance in the intravitreus cavity, ocular globe or any other area which allows the injection of a device according to the invention and contains injured tissue. A preferred implantation route is the injection in the intravitreous cavity, especially for treatment of degenerative eye disorders.

In this regard, the invention also provides a method of reducing an ocular disease comprising administering intraocularly to a subject in need of such treatment a composition comprising encapsulated cells which produce a polypeptide biologically active for reducing the ocular disease. The polypeptide is preferably a neurotrophic or anti-angiogenic polypeptide as defined above. The ocular disease can be any ocular disease such as a tumor or tumors, ocular degeneration, retinopathies, retinitis and the like.

In a preferred embodiment, age-related macular degeneration (AMD) can be reduced using the methods and composition of the present invention. This has been demonstrated herein using the congenic Royal College of Surgeons (RCS) rat strain which represents the closest and most recognized rodent model for retinal pigment epithelium (RPE) linked retinopathies (22, 23). RCS rats have a recessive hereditary retinal dystrophy evident by the third postnatal week. This dystrophy is characterized by a progressive degeneration of RPE cells and a secondary loss of photoreceptor cells by apoptosis (24, 25). In the dark-eyed rat strain RCS p+, retinal dystrophy progresses to a complete photoreceptor cell degeneration at the age of 2 months (22, 23, 26). Cell degeneration is related to a deficiency of the phagocytosis of photoreceptor outer segments by RPE cells and is accompanied by a significant decrease in the production of the basic fibroblast growth factor (FGF-2; 18 kDa) in the retina (27). The results presented in the examples demonstrate that the instant invention can be used to treat, reduce or alleviate photoreceptor degeneration and AMD. In particular, a significant rescue of photoreceptor cells is achieved in vivo upon intraocular administration of the composition of the present invention. The capacity of the encapsulated cells of this invention to rescue photoreceptor cells was further demonstrated in the dystrophic RCS retina.

In another particular embodiment, the present invention thus provides an efficient method of reducing photoreceptor cells degeneration comprising administering intraocularly to a subject in need of such treatment a composition comprising encapsulated cells which produce a biologically active anti-angiogenic polypeptide. Preferably, the biologically active anti-angiogenic polypeptide is an endostatin polypeptide or an FGF polypeptide.

Other retinopathies include, for instance, circinate retinopathy, diabetic retinopathy, hypertensive retinopathy, leukemic retinopathy, pigmentary retinopathy, sickle cell retinopathy and the like, which can also be reduced using the present invention.

The invention also relates to a composition comprising encapsulated cells which produce an endostatin or an FGF polypeptide. More preferably, some of the encapsulated cells contain a recombinant nucleic acid construct encoding an endostatin or an FGF polypeptide, preferably a human endostatin or a human FGF. As explained above, the composition comprises preferably at least $10^4$ cells encapsulated in a biocompatible jacket. A particular example is represented by a composition comprising cells containing a nucleic acid construct encoding human FGF-2. In this respect, the cytoplasmic 18 kDa form of FGF-2 can be secreted despite the absence of a hydrophobic secretory signal sequence. This protein is exported presumably via a mechanism of exocytosis independently of the endoplasmic reticulum-Golgi complex pathway (28–31). FGF-2 is either stored extracellularly by associating with heparin sulfate proteoglycans or binds with high affinity to membranous tyrosine kinase receptors where it exerts pleiotropic effects on cell growth, differentiation, morphogenesis, and cell repair (32). As demonstrated previously, human FGF-2 (hFGF-2) can transiently delay photoreceptor cell degeneration when injected intravitreally or subretinally (33).

The invention thus provides compositions or methods which allow the intraocular production and secretion of this trophic factor by encapsulated cells, in particular mouse fibroblasts.

The invention shows, for the first time, that transplantation of xenogeneic polypeptide-secreting cells, encapsulated in a biopolymer, into the vitreous body can promote the survival of photoreceptor cells in the retina in vivo. As compared to other cell therapy protocols, this technique has the advantage to avoid possible implant-linked adverse side effects on the retina by surgically retrieving obsolete microcapsules. The transfer of encapsulated cells producing trophic factors thus represents a new approach to treat, reduce or alleviate neurodegenerative retinopathies. The invention can also be used to deliver biologically active polypeptides to animals, in order to study their properties (stability, activity, etc.) or metabolism, or as a treatment.

Other advantages and embodiments of this invention will be disclosed in more details in the following experimental section, which should be regarded as illustrative and not limiting the scope of the invention. All references cited in the present application are incorporated herein by reference.

EXAMPLES

Materials and Methods

1. Production and culture of human FGF-2-secreting cells

To produce human FGF-2-secreting fibroblast cells PS-FGF18 (FGF-18), mouse fibroblasts (NIH3T3) were stably transfected with the bicistronic plasmid pSFGF18 (6.43 kb) which was constructed on the basis of the vector pEN (43). The plasmid pSFGF18 contains the pVC-derived Sma I-Nco I fragment (44), encoding the amino-terminal secretion signal peptide (PS) of the vascular endothelial growth factor (VEGF), which was inserted into the Sma I-Nco I restriction sites of pF18EN (45). The vector further contains the upstream enhancer/promoter sequence of the cytomegalovirus (CMV) followed by the chimeric VEGF-hFGF-2 gene (Genbank accession # of the human FGF-2 cDNA: M27968), the downstream internal ribosomal entry site of the encephalomyocarditis virus, the neomycine resistance gene, the SV40 polyadenylation signal sequence, the IVS2b intron of the rabbit β-globin gene, and the ampicillin resistance gene. Thus, plasmid transcription gives rise to a bicistronic mRNA containing the coding sequences of hFGF-2 and aminoglycoside phosphotransferase. To obtain NIH3T3-P16 cells (P16), mouse fibroblasts were stably transfected with a modified pRPSFEN plasmid which lacks the hFGF-2 transgene sequence. Cells were selectively cultured in a humid $CO_2$ incubator at 37° C. using 75 $cm^2$ flasks (Techno Plastic Products, Switzerland). The Dulbecco's Modified Essential Medium DMEM/F12 (growth medium; Life Technologies, France) was enriched by 10% decomplemented Australian fetal calf serum (FCS; Life Technologies, France) and contained a pre-fabricated mixture of antibiotic-antimycotics (Life Technologies, France; final concentrations: 100 units/ml penicillin, 0.1 mg/ml streptomycin, 0.25 mg/ml Amphotericin B) as well as 0.7 mg/ml geneticin (G418; Life Technologies, France).

2. Encapsulation and Cell Viability

Trypsinized PS-FGF18 and P16 cells were suspended in the growth medium containing 10% FCS plus antibiotic-antimycotics (Life Technologies, France) and mounted by capillarity into Dialox-treated 5-cm-long AN69 polymer fibers (50 kDa cut-off 300 μm external diameter, 200 μm internal diameter; Hospal R & D, Meyzieu, France). Fibers were heat-sealed at both ends and kept in culture for 1 day to allow cell aggregation and attachment to the polymer. Then, the capsules were segmented into 1.5 mm. or 4.0 mm microcapsules and were kept in culture for at least 14 days prior to transplantation. NIH3T3-P16 and NIH3T3 PS-FGF18 fibroblasts were released from twenty-four 4.0-mm-long capsules by trypsinization after 2, 15, 30, and 60 days in culture (n=6 for each cell type and time point). Cell viability was determined by trypan blue exclusion in growth medium (0.2% Trypan blue; Life Technologies, France) using a hemocytometer. Eight 1.5 mm microcapsules filled with either NIH3T3-P16 or NIH3T3 PS-FGF18 cells were explanted after 45 days (n∝for each cell type). Similarly, a microcapsule with NIH3T3-P-16 cells and a microcapsule filled with NIH3T3 PS-FGF18 cells were explanted at 90 days post-transplantation. Microcapsules were trypsinized in phosphate-buffered saline (PBS) for 20 mm at 37° C., rinsed in growth medium, and opened to release cells for trypan blue exclusion assays.

3. Biopolymer Permeability and Bioassay

Three 1.0-cm-long capsules were pre-incubated for 24 h with growth medium containing 10% FCS plus antibiotic-antimycotics and subsequently filled with 125 ng recombinant hFGF-2. Following another 24 h incubation in growth medium at 37° C., the concentration of soluble and substrate-bound protein released from capsules was measured by ELISA. Microcapsules with a length of 1.6 mm and 4.0 mm, which were either empty (n=6, 4.0 mm) or filled with NIH3T3 PS-FGF18 or NIH3T3 P16 cells and kept in culture for 15, 30, or 60 days (n=6 per cell type and time point), were transferred to 6-well TPP culture plates (1 microcapsule/well; Techno Plastic Products, Switzerland) containing adherent NIH3T3 fibroblasts (5×104/well). After 10 days of co-culturing in growth medium containing 10% FCS plus antibiotic-antimycotics at 37° C. 5% $CO_2$, the NIH3T3 cell density was determined with a hemocytometer and compared to untreated NIH3T3 fibroblast cultures. The cell proliferation rate under the experimental conditions was analyzed statistically using the Mann-Whitney U-test.

4. hFGF-2 production determined by Western Blotting and Enzyme-Linked Immuno-Sorbant Assay (ELISA)

Stably transfected fibroblasts were sonicated on ice (3×2 sec; Branson sonifier 450) in 20 ml PBS plus 2% sodium dodecyl-sulfate (SDS) and denatured in 40 ml Laemmli buffer at 85° C. for 5 min. Both recombinant bacterial hFGF-2 (10 ng) and crude cell extract proteins (5×10$^5$ cells) were separated by size in a 12% denaturing SDS-polyacrylamide protein gel (Protogel; National Diagnostics, Atlanta, USA) and blotted onto an Immobilon P membrane (Millipore, France). After overnight incubation of the membrane with primary polyclonal rabbit anti-hFGF-2 antibodies (1/200; Santa Cruz Biotechnology, USA) in 5% fat-free milk powder/TBST (10 mM Tris-HCl pH 8, 150 mM NaCl, 0.05% (v/v) Tween-20®), the hFGF-2 protein was visualized by means of an ECL kit (Amersham, France) according to the manufacturer's instruction. The secretion of hFGF-2 from 106 NIH3T3 PS-FGF18 cells, cultured in 6-well TPP culture plates for 24 h in growth medium at 37° C./$CO_2$, was measured by a Human FGF Basic ELISA kit (Quantikine; R&D Systems, Abingdon, UK) according to the manufacturer's instructions. Protein release from 1.0-cm-long capsules was determined similarly after they were filled with 125 ng recombinant hFGF-2 protein and incubated in TPP culture plates with growth medium for 24 h at 37° C. Detachment of hFGF-2 from the culture plate substrate was carried out at 37° C. by successive 20 min incubation steps with 2 M NaCl, 20 mM sodium acetate (pH 4.5) and 2 M NaCl, 20 mM HEPES pH 7.5.

5. Intravitreal Transplantation 1.5-mm-long microcapsules, filled with either NIH3T3-P16 or NIH3T3 PS-FGF18 cells, were kept in culture for 14 days. Leak-proof capsules were then transplanted into the vitreous cavity of 29 globes from 21-day-old RCS p+ rats (n=21 rats; kindly provided by Dr. M. M. LaVail, UCSF, San Francisco, USA). For transplantation, these rats were anesthetized by an intraperitoneal injection of 100 mg/kg ketamine (Kétalar; Laboratoire Substantia, France). Topical anesthesia by oxybuprocaine chlorydrate (Cébésine, Laboratoire Chauvin, France) was applied onto the cornea to eliminate the eyelid reflex. Head and eyelid were cleaned with 70% ethanol prior to an external canthotomy of the eye. The temporal superior region of the conjunctival tissue was cut at 1 mm from the limbus. The ocular globes were perforated with a surgical monofilament needle (10/0). The perforation was enlarged with a surgical scalpel to 1 mm in length to allow the intravitreal transfer of a 1.5 mm microcapsule filled with either NIH3T3-P16 (unable to produce and to release hFGF-2) or NIH3T3 PS-FGF18 cells (producing and secreting the recombinant 18 kDa hFGF-2 isoform). The canthotomized eyelids were closed with 3 stitches using a vicryl filament (8/0). The treated eyes were finally covered with a paste of Sterdex (Laboratoire Martinet, France) containing dexamethasone and oxytetracycline. Operated rats of the same experimental group were kept together for 45–90 days under standard animal housing conditions at an illuminosity between 0 Ix (12 hrs dark) and 150 Ix (12 hrs light) with food and water being available ad libitum. Both the transplanted and the control animals were clinically examined biomicroscopically each day.

In the first experimental series (intravitreous transplantation), four experimental groups of rats were constituted following a procedure of randomization. Group I (6 rats) and group II (4 rats): the eyes were histologically analyzed at 90 days post-transplantation; group III (6 rats) and group IV (5 rats): the eyes were studied histologically at 45 days post-transplantation. In all groups, each eye was randomly chosen by the surgeon for microcapsule transplantation. In groups I and III, microcapsules containing hFGF-2-producing cells were randomly allocated to the eyes whereas the contralateral eyes of the same rats received microcapsules containing NIH3T3 P16 cells which are unable to release recombinant hFGF-2. In the groups II and IV, hFGF-2-releasing microcapsules were randomly allocated to the eyes while the contralateral eyes of the same rats did not receive any treatment. One eye of group I which received a microcapsule filled with NIH3T3 PS-FGF18 cells presented endophthalmitis. In group III, analyzed at 45 days post-transplantation, microcapsules containing NIH3T3-PS-FGF18 cells were randomly allocated to six eyes whereas the contralateral eyes received encapsulated NIH3T3 P16 cells. In group IV, one rat displayed unilateral endophthalmitis which was confined surprisingly to the untreated contralateral eye. The treated eye of the same rat could not be analyzed histologically due to difficulties encountered during the cryostat cutting procedure. In total, 3 eyes were excluded from the statistical analysis. Thus, out of 42 eyes (n=21 rats) involved initially in our first experimental series, only 39 eyes could be subjected to detailed histological and statistical analyses. A second experimental series involved 5 rats: each rat received subretinal transplantation of a microcapsule filled with either NIH3T3 PS-FGF18 (n=3) or NIH3T3-P16 cells (n=2). The contralateral eyes had no surgical treatments. This type of implantation caused surgically induced local tissue necrosis. One of the two eyes which had a subretinal transplantation of a microcapsule containing NIH3T3-P16 cells presented endophthalmitis.

6. Tissue Staining and Histological Analysis

All treated rats were subjected to pupillary reflex testing and enucleated post-mortem after $CO_2$ asphyxia. Ocular globes were embedded in Tissue-Tek O.C.T. compound (4583; Miles Diagnostics, Elkhart, USA), immediately frozen in dry ice-cooled isopentane, and cut on a cryotome (Leica cryocut 3000). Serial 16-mm-thick sections were mounted onto glass slides that were pre-treated with 2% (v/v) 3-aminopropyl-triethoxysilane in acetone and post-fixed for 20 min with 2% (w/v) paraformaldehyde in 0.1 M phosphate buffer pH 7.4 at 4° C. After toluidine blue staining and incubation for 5 min in 5% ammonium heptamolybdate in PBS, sections were dehydrated in ethanol and coverslipped in Eukitt (O. Kindler GmbH, Freiburg, Germany). In each eye, the number of photoreceptor cell layers was counted on sections about 50 mm apart under a light microscope at a 400-fold magnification. In each section evaluated, the number of photoreceptor cell rows in the outer nuclear layer was determined at field points being 125 mm apart. If a field point revealed a row number with more than 4 photoreceptor cell layers, it fulfilled the criterion for photoreceptor cell rescue. The field of delayed cell degeneration was determined on two-dimensional schematic representations of the retina. Differences in the rescued retinal area between the experimental groups which received microcapsules, filled with either NIH3T3-P16 (n=12 eyes) or NIH3T3 PS-FGF18 cells (n=19 eyes), were analyzed statistically using the Mann-Whitney U-test. After elimination of the four endophthalmic eyes and the one eye which was damaged during sectioning, 39 eyes out of 42 (n=21 rats) were available for the counting of photoreceptor nuclei rows in the outer nuclear layer of the rat retinas.

7. Immunohistochemistry

Ocular globes were fixed for 2 days in Davidson fixative (Prolabo, France) and embedded in parafin. Serial 5-mm-thick sections were cut with a microtome and mounted onto DAKO ChemMATE capillary gap microscope slides (DAKO, France). After an exposure to 56° C. for 2 days, the slides were boiled for 10 min in 800 ml 0.1 M citric acid (adjusted to pH 6 with 2 N HCl) using a microwave oven (750 W). Then, the solution containing the slides was left at ambient temperature during 30 min before the sections were rinsed in PBS. Following 5 min incubation in TBS (0.05 M Tris-HCl, 0.15 M NaCl, pH 7.6) and a rinse step in TBS plus 1% bovine serum albumin (BSA), the sections were exposed to 10 ng/ml monoclonal mouse anti-bovine basic FGF IgGs (type II; Upstate Biotechnology; Lake Placid, N.Y., USA) in DAKO ChemMATE Antibody Diluent (DAKO, France) for 1 h at room temperature. After successive washing steps in 0.05 M Tris-HCl (pH 6) and TBS plus 1% BSA, immunostaining was carried out with biotinylated secondary IgGs, horseradish peroxidase, and diaminobenzidine (DAB) using the ChemMATE Detection kit (DAKO, France). The DAB-stained sections were subsequently colorated with Harris' hematoxyline (Reactifs RAL, Paris, France) for 1 min and rinsed in a saturated aqueous solution of lithium carbonate (Prolabo, France). Then, the sections were dehydrated in ethanol and rinsed with toluene and xylene before they were coverslipped in Eukitt.

Results

8. Viability of Encapsulated Fibroblasts

The viability of encapsulated NIH3T3-P16 and NIH3T3 PS-FGF18 cells was examined first under culture conditions. In 4.0 mm microcapsules, these cells typically reaggregated and attached to the biomaterial AN69 within 24 hours when kept in growth medium (FIG. 1(1)). As determined at 15 days post-encapsulation, both cell types filled the lumen of the fibers by reaching an average density of $2.16 \times 10^5$ cells per microcapsule (FIG. 1 (2)). At this time point, an average 75% of NIH3T3 PS-FGF18 cells and 67% of NIH3T3-P16 cells were viable inside the microcapsules, as determined by trypan blue exclusion (FIG. 2). When encapsulated cells were cultured for 30–60 days, cell survival declined to 60–65% in NIH3T3 PS-FGF18 cells and to 2% in NIH3T3-P16 cells (FIG. 2).

Figure 1:
FIG. 1 are photographs of the microencapsulation and transplantation of encapsulated NIH3T3 PS-FGF18 cells to the eye of a RCS p+ rat. A-B) Cells are packed into a 1.5 mm microcapsule and kept in culture for 1 day (1) and 14 days (2) prior to transplantation. As seen through the lens, a 1.5 mm microcapsule (arrow) was implanted into the vitreous cavity (3). (4) is the explanted 1.5 mm microcapsule after being in the vitreous cavity for 90 days. Microcapsule diameter: 300 μm. Scale bars: 200 μm (1, 2), 1 mm (3), 100 μm (4).

After 1.5 mm microcapsules with an internal volume of 0.3 ml were kept in culture for 14 days, leak-proof capsules were selected and subsequently transplanted into the vitreous cavity of RCS rats (FIG. 1(3)). Cell survival was measured by trypan blue exclusion at 45 days and 90 days post-transplantation. 58% of NIH3T3 PS-FGF18 cells and 69% of NIH3T3-P16 cells were viable in microcapsules at 45 days. Their cell number varied between $2 \times 10^3$ and $10^4$ cells per microcapsule. A few NIH3T3 PS-FGF18 cells retained their ability to attach to the culture plate substrate after being released from the capsules. As found in a microcapsule explanted after 90 days in oculo, 29% of NIH3T3 PS-FGF18 cells were viable. On the other hand, NIH3T3-P16 cells had changed their morphological appearance at this time point and had fissioned to apoptotic bodies. On toluidine blue-stained 16-mm-thick sections cut through microcapsules embedded in the vitreous body, a homogeneous distribution of NIH3T3 PS-FGF18 cells was found. Whereas in transplanted microcapsules filled with NIH3T3-P16 cells, the cells formed aggregates which caused intercellular gaps.

9. Expression of hFGF-2

The expression of the hFGF-2 transgene by encapsulated and transplanted NIH3T3 PS-FGF18 cells was verified by immunohistochemistry. As seen on 5-mm-thick sections through a microcapsule filled with NIH3T3 PS-FGF18 cells at 90 days post-transplantation, hFGF-2-like immunoreactivity (IR) was detected in the cytoplasm of about one third of encapsulated cells (FIG. 9 (5)). Immunohistochemical staining of the inner and outer nuclear layers of the retina as well as the RPE cell layer serve as a positive control for the antigen-specificity of the antibody used (FIG. 9 (1)). Unlike the cytoplasmic hFGF-2-IR of encapsulated cells, the retinal cells appear to have mainly nuclear FGF-2 staining.

10. Release of hFGF-2 from microcapsules

The production of hFGF-2 in cultured NIH3T3 PS-FGF18 cells was visualized and quantified by Western blotting and ELISA. On immunoblots, cellular hFGF-2 has an apparent molecular weight of 18 kDa which corresponds in size to the recombinant hFGF-2 protein (FIG. 3). In NIH3T3-P16 cells, in turn, the concentration of the endogenous 18 kDa form of FGF-2 was below the threshold of detection. As quantified by ELISA, NIH3T3 PS-FGF18 cells secrete an average of 68.7 pg±2.3 (s.e.m.; n=6) hFGF-2/10$^6$ cells within 24 h (FIG. 4). This value represents the overall level of extracellular hFGF-2 whereas 96% of which was found to adhere to the culture plate substrate. The permeability of the biopolymer membrane for the hFGF-2 protein was further verified in 1.0-cm-long capsules. In these capsules, 2% of hFGF-2 diffused through the biopolymer membrane during 24 hrs. at 37° C. As determined by a bioassay, the quantity of released hFGF-2 is sufficient to stimulate cell proliferation. During a co-culture period of 10 days with either encapsulated NIH3T3-P16 cells or empty microcapsules, NIH3T3 cells grew from 5×10$^4$ cells to 6.5×10$^6$ cells per well (FIG. 5). A similar proliferation rate was found in untreated adherent NIH3T3 cell cultures. When NIH3T3 cells were exposed for 10 days to NIH3T3 PS-FGF18-filled capsules kept in culture for 15–60 days, a significant increase in NIH3T3 cell proliferation by 35%±2.1 (s.e.m.; 1.5 mm capsules, n=18) and 58%±2.6 (s.e.m.; 4.0 mm capsules, n=18) was observed as compared to NIH3T3-P16 capsules (P=0.001, Mann-Whitney U-test).

11. Photoreceptor Cell Rescue and FGF-2-immunoreactivity

The ability of NIH3T3 PS-FGF18-filled microcapsules to delay photoreceptor cell degeneration was studied by analyzing the number of photoreceptor cell layers in the RCS p+ rat retina. At postnatal day 21, the RCS retina normally shows an average number of 10 photoreceptor cell layers (FIG. 6 (1)). After 45 days, these layers are typically reduced to 1–2 rows in untreated eyes (FIG. 6 (2)). At 45 and 90 days post-transplantation, NIH3T3-P16 microcapsule implants caused a delayed photoreceptor cell degeneration covering an average retinal area of 0.08 mm2±0.04 and 0.025 mm2±0.03, respectively (s.e.m.; n=6; Table I).

FIG. 7 shows a graphical representation of an eye with a NIH3T3-P16 microcapsule which had one of the largest surface (0.15 mm$^2$) fulfilling the criterion for delayed cell degeneration (described in Materials and Methods; FIG. 7 (2), Table I). In the majority of ocular bulbi with NIH3T3-P16 microcapsules as well as in all the untreated eyes, the number of photoreceptor cell layers was reduced to a single cell row. Eyes which received NIH3T3 PS-FGF18 microcapsules retained 5–6 photoreceptor cell layers in the retina close to the implant at 45 days as well as at 90 days post-transplantation (FIG. 6 (3)). A rescued area of 2.08 mm$^2$±0.72 (s.e.m.; n=10), observed at 45 days post-transplantation, was restricted to the retinal zone at the vicinity of the microcapsule and was significantly higher than that observed in untreated control eyes (P=0.001, Mann-Whitney U-test; Table I). The maximal rescue effect amounted to 4 mm$^2$ or 10% of the entire retinal surface and represents 10 times the region covered directly by the microcapsule (FIG. 7(1)). Similarly, an average retinal area of 0.95 mm$^2$±0.22 (s.e.m.; n=9) was rescued by 90-day-old implants. This local rescue effect is significantly lower than that found at 45 days post-transplantation but is significantly higher than the effect of NIH3T3-P16 microcapsules on the survival of photoreceptor cells (P<0.05, Mann-Whitney U-test; Table I). In untreated eyes, no more than 3 photoreceptor cell layers were found in the retina at both time points (FIG. 6 (4)).

Rosette formation and abnormal thickness of the retina were detected in 2 out of 31 treated globes which received encapsulated NIH3T3 PS-FGF18 or NIH3T3-P16 cells (FIG. 8). Furthermore, posterior cataracts were apparent in 3 eyes with NIH3T3-P16 microcapsules as well as in 2 globes with encapsulated NIH3T3 PS-FGF18 cells. Three treated eyes showed signs of surgically induced infection leading to ocular atrophy in the experimental series. In 29 ocular globes, the microcapsules were entirely intravitreal and revealed neither apparent graft rejection by intraocular macrophage infiltration nor fibrous formation around the microcapsule. In the 2 ocular globes displaying rosettes, the microcapsules rested upon the inner surface of the retina.

The endogenous production of FGF-2 in the RCS retina was visualized by immunohistochemistry. In the normal retina of a 3-month-old albino RCS p-rdy+ rat, mainly nuclear FGF-2-IR was apparent in some cells of the inner nuclear layer as well as in all photoreceptor cells of the outer nuclear layer (FIG. 9 (2)). Cell nuclei of RPE cells also revealed strong immunostaining. In dystrophic 111-day-old RCS p+ rats, however, FGF-2-IR was found in some cells of the inner nuclear layer (FIG. 9(3)), but it was absent from degenerating photoreceptor cells. In several age-matched RCS rats which received NIH3T3 PS-FGF18 microcapsules, the locally rescued photoreceptor cells were also devoid of FGF-2-IR whereas the inner nuclear layer still revealed some immunostained cells (FIG. 9 (4)).

CLONING THE GENE ENCODING MOUSE ENDOSTATIN INTO CHO CELLS

Sequences encoding endostatin protein were amplified by PCR using Goldstar polymerase (Eurogentec). Primers endo s:

(3'-CCGACTTTCAGGACTACTCATACTTAAGGGTA-CCAAA-5') (SEQ ID NO:4) containing a linker with NcoI and endo s his rev:

(3'GTACTGGAGAAAGAGGTTTCGGCCGTCTCCTA-GCGTAGTGGTAGTGGTA
GTGCACATCGGCGCCAAA-5') (SEQ ID NO:5), containing his tag and linker with SacII were used. Mouse cDNA was used as a template.

For a 50 µl final volume, 1 µl of the cDNA template, 0.5 µg of each primer, 0.2 mM DNTPs, 5 µl 10× Goldstar Reaction Buffer (from Eurogentec), 1.5 mM MgCl$_2$ and 2.5 Units Goldstar Polymerase (from Eurogentec) was used. PCR was carried out for 30 cycles using the following parameters: 94° C. denaturation for 1 minute; 62° C. annealing for 1 minute; and 72° C. annealing for 1 minute.

The product of the amplification (540 Kb) was sequenced on both strands using a Perkin Elmer Kit.

After completion, the product of the amplification was gel purified using Gene-Clean (Boi 101, La Jolla) and the linkers were digested with the appropriate enzymes and then again purified using Gene-Clean.

The gene fragment was ligated into a PRCEN expression vector in fusion with the VEGF peptide signal and tag HA (Hemaglutinine).

The resultant *E.coli* clones were selected and plasmid preparations (pRCEN endo) of clones were obtained and sequenced.

Stable CHO clones were obtained by transfection with pRCEN endo (2 μg) using a fuGENE™ 6 transfection reagent (Boehringer Mannheim) in a 60 mm dish containing 5 ml of MEM (Minimum essential Medium, Gibco, BRL) complemented with 5% FCS, 1% Glutamine, 1% amphotericine B and 0.5% Gentamicine). 24 hours later the cells were trypsinized and transferred into 3 100 mm dishes in the presence of G418 (1 mg/ml). The cultures were maintained for 2 weeks in the presence of G418, and 12 clones were picked up and transferred into 24-well plates before cultivation in larger dishes.

The construct of plasmid pRCEN1-Endo is shown in FIG. 10. The various sequences used to construct this plasmid such as the peptide signal sequence VEGF, HA and endo are shown in FIG. 11.

Western immunoblotting was then performed using a conditioned medium. The cells were then precipitated with TCA and the cell lysates of the different clones were analyzed by western immunoblotting using polyclonal anti-HA antibody (Eurogentec). The Western blot is shown in FIG. 12.

In the present invention, a novel intravitreal cell therapy approach for an experimental treatment of retinal dystrophies is disclosed. The therapeutic transgene hFGF-2 was transferred to the ocular bulbi via stably transfected and encapsulated NIH3T3 PS-FGF18 fibroblasts. These cells as well as hFGF-negative fibroblasts (NIH3T3-P16) can adhere to the biopolymer and proliferate inside the microcapsules. Fibroblasts which produce no or only a low level of hFGF-2 showed limited cell survival under encapsulation conditions. These cells typically continue to proliferate inside microcapsules under culture and in oculo conditions, grow to confluency, and eventually undergo cell apoptosis. Due to the anti-apoptotic action of FGF-2 (46), however, cell apoptosis can be impeded by the intracellular production of FGF-2. Indeed, encapsulated NIH3T3 PS-FGF18 cells, which produce and secrete a high level of the 18 kDa protein isoform of hFGF-2, revealed long-term cell viability both under culture condition and inside the vitreous cavity. Due to the hydrophobic VEGF secretory signal peptide, linked to the amino-terminus of the protein, hFGF-2 secretion is favored by the endoplasmic reticulum-Golgi complex secretory pathway. As shown by immunohistochemistry on encapsulated NIH3T3 PS-FGF18 fibroblasts at 90 days post-transplantation, about 30% of these cells continue to produce hFGF-2 which seems to be concentrated in the cytoplasm. Using a bioassay, it was confirmed that encapsulated NIH3T3 PS-FGF18 fibroblasts can stimulate cell proliferation, with a dose-response effect, in a capsule/NIH3T3-P16 cell co-culture system. This finding demonstrated indirectly that secreted hFGF-2 can diffuse through the biopolymer membrane of the capsule.

The membrane permeability for hFGF-2 has also been observed in vivo. When transplanted into the vitreous cavity, microcapsules filled with hFGF-2-secreting fibroblasts provoked a delay of photoreceptor cell degeneration. At 45 days post-transplantation, this cell rescue effect was dearly observed in up to 10% of the retinal surface. The average area rescued by 90-day-old microcapsules, however, is about half of the size of that detected at 45 days post-transplantation. As the viability of encapsulated hFGF-2-producing fibroblasts gradually declines in vivo, photoreceptor cell degeneration may have resumed at 90 days post-transplantation.

In ocular globes with encapsulated NIH3T3-P16 cells, the photoreceptor cell rescue effect was minimal, indicating that secreted hFGF-2 is responsible for the delay of photoreceptor cell degeneration. This observation further shows that the surgical trauma caused by the microcapsule implantation did not induce cell rescue. In contrast, in other experimental settings such as intravitreal injections of PBS versus hFGF-2, control animals displayed a significant local rescue effect (33). Although hFGF-2-releasing microcapsules lead to a local delay of photoreceptor cell degeneration in 66 and 111-day-old RCS p+ rats, the rescued retinal photoreceptor cells had an undetectable level of FGF-2-immunostaining. This finding is in line with a reduced level of FGF-2 protein in overall retinal preparations of RCS rats (27). Since, after the onset of the retinal degeneration, a transient increase of FGF-2 concentration can occur in photoreceptor cells of RCS rats as compared to those of normal RCS rdy+ rats (47), it must be concluded that in the experiments the rescued photoreceptor cells failed to regain the ability of producing endogenous FGF-2. Thus, the rescue effect of photoreceptor cells seems to depend entirely on the presence or absence of exogenous FGF-2 in the retina.

Under in vivo conditions the hFGF-2 protein released by the microcapsule diffuses through the vitreous humor and is presumably absorbed by ganglion and Müller cells in the retina close to the microcapsule. As recently described, exogenous FGF-2 can stimulate the expression of the FGF-2 gene in cultured Müller cells (48). In adult RCS rats with dystrophic retinas, a significant FGF-2-IR in large cell bodies of the inner nuclear layer which may correspond to Müller cells was also found. Since these cells span the entire retina, an hFGF-2-stimulated increase of the production and secretion of endogenous FGF-2 may help to slow photoreceptor cell degeneration. Moreover, FGF-2 inhibits the production of cytotoxic nitric oxide in RPE cells which can affect indirectly the survival of photoreceptor cells (49–51). It cannot be excluded that a direct effect of hFGF-2 on photoreceptor cells and/or RPE cells after diffusion throughout the different retinal layers.

As it has been shown previously, FGF-2 can potentially induce tumor-like cell proliferation (52). Although any signs of tumor formation was not found, a few photoreceptor cell rosettes were detected in two out of the 31 ocular globes analyzed. This abnormality is independent of the type of microcapsules implanted, suggesting that the malformation is caused by the surgical trauma. Despite the local application of corticoids and antibiotics, three eyes developed endophthalmitis, two in the first experimental series and one in the second series. Since ocular atrophy was not restricted to eyes which received a particular type of encapsulated cells, surgically-induced infection may be at the origin of endophthalmitis. It was noticeable that in one eye of the first experimental series, endophthalmitis occurred in an untreated eye, suggesting that aseptic procedures should be improved to avoid this iatrogenic complication. Moreover, all treated globes were devoid of microcapsule-mediated fibrosis or hyperacute macrophage cell infiltration into the vitreous cavity, indicating that the biomaterial did not provoke any cell-mediated immune response. Within microcapsules, however, fibroblasts gradually undergo apoptosis. Since the 50 kDa cut-off pore size of the AN69 biopolymer hampers the penetration of IgMs, membrane attack complexes and C1 fraction of the complement (53), cell death inside the microcapsule was probably not provoked by the host complement system. These findings indicate that the biomaterial is not immunogenic per se and sufficiently protects hFGF-2-secreting fibroblasts against cell death mediated by immune responses.

Besides using the hFGF-2 protein, other well characterized cell lines can be used which are capable of releasing other trophic factors. For example, cell lines can be engineered which produce the ciliary neurotrophic factor (CNTF) and/or the glial cell line-derived neurotrophic factor (GDNF) which are indispensable for their own proliferation as well as for photoreceptor cell survival.

The use of inducible promoters such as the tetracycline regulation cassette which allows to experimentally modulate transgene transcription is obviously an additional potential protection against unpredictable iatrogenic effects.

Furthermore, the present invention is not limited to the use of AN69. Other biomaterials which are, first of all, as efficient as AN69 in terms of limiting humoral and cellular immune reactions and, in particular, the activation of the complement system, and secondly, allow a better diffusion of therapeutic molecules can be used.

REFERENCES

1. Chick, W. L., Perna, J. J., Lauris, V., Low, D., Galietti, P. M., Whitemore, A. D., Like, A. A., Colton, C. K., & Lysaght, M. J. (1977) Science 197, 780–782.
2. Lim, F. & Sun, A. M. (1980) Science 210, 908–910.
3. Fan, M. Y., Lum, Z. P., Fu, X. W., Levesque, L., Tai, I. T., & Sun, A. M. (1990) Diabetes 39, 519–522.
4. Lacy, P. E., Hegre, O. D., Gerasimidi-Vazeou, A., Gentile, F. T., & Dionne, K. E. (1991) Science 254, 1782–1784.
5. Zondervan, G. J., Hoppen, H. J., Pennings, A. J., Fritschy, W., Wolters, G., & van Schilfgaarde, R. (1992) Biomaterials 13, 136–144.
6. Al-Hendy, A., Hortelano, G., Tannenbaum, G. S., & Chang, P. L. (1995) Hum. Gene Ther. 6, 165–175.
7. Liu, H. W., Ofosu, F. A., & Chang, P. L. (1993) Hum. Gene Ther. 4, 291–301.
8. Koo, J. & Chang, T. M. S. (1993) Int. J. Artif. Organs 16, 557–560.
9. Sagen, J., Wang, H., Tresco, P. A., & Aebischer, P. (1993) J. Neurosci. 13, 2415–2423.
10. Joseph, J. M., Goddard, M. B., Mills, J., Padrun, V., Zurn, A., Zielinski, B., Favre, J., Gardaz, J. P., Mosimann, F., Sagen, J., Christenson, L., & Aebischer, P. (1994) Cell Transplant. 3, 355–364.
11. Aebischer, P., Schluep, M., Deglon, N., Joseph, J. M., Hirt, L., Heyd, B., Goddard, M., Hammang, J. P., Zum, A. D., Kato, A. C., Regli, F., & Baetge, E. E. (1996) Nature Medicine 2, 696–699.
12. Emerich, D. F., Winn, S. R., Christenson, L., Palmatier, M. A., Gentile, F. T., & Sanberg, P. R. (1992) Neurosci. Behav. Rev. 16, 437–447.
13. Emerich, D. F., Lindner, M. D., Winn, S. R., Chen, E.-Y., Frydel, B. R., & Kordower, J. H. (1996) J. Neurosci. 16, 5168–5181.
14. Emerich, D. F., Winn, S. R., Hantraye, P. M., Peschanski, M., Chen, E.-Y., Chu, Y., McDermott, P., Baetge, E. E., & Kordower, J. H. (1997) Nature 386, 395–399.
15. Tresco, P. A., Winn, S. R., Tan, S., Jaeger, C. B., Greene, L. A., & Aebischer, P. (1992) Cell Transplant. 1, 255–264.
16. Hoffman, D., Breakfield, M., Short, P., & Aebischer, P. (1993) Exp. Neurol. 121, 100–106.
17. Aebischer, P., Goddard, M., Signore, A. P., & Timpson, R. L. (1994) Exp. Neurol. 126, 151–158.
18. Lindner, M. D., Winn, S. R., Baetge, E. E., Hammang, J. P., Gentile, F. T., Doherty, E., McDermott, P. E., Frydel, B., Ullman, M. D., Schallert, T., & Emerich, D. F. (1995) Exp. Neurol. 132, 62–76.
19. Martinez, G. S., Campbell, A. J., Reinken, J., & Allan, B. C. (1982) Am. J. Ophthalmol. 94, 181–189.
20. Klein, B. E. & Klein, R. (1982) Arch Ophthalmol. 100, 571–573.
21. Kahn, H. A., Leibowitz, H. M., Ganley, J. P., Kini, M. M., Colton, T., Nickerson, R. S., & Dawber, T. R. (1977) Am. J. Epidemiol. 106, 17–32.
22. Bok, D. & Hall, M. O. (1971) J. Cell Biol. 49, 664–682.
23. LaVail, M. M., Sidman, R. L., & Gerhardt, C. O. (1975) J. Hered. 66, 242–244.
24. LaVail, M. M. (1981) Invest. Ophthalmol. Visual Sci. 21, 638–657.
25. Tso, M. O., Zhang, C., Abler, A. S., Chang, C. J., Wong, F., Chang, G. Q., & Lam, T. T. (1994) Invest. Ophthalmol. Vis. Sci. 35, 2693–2699.
26. Sheedlo, H. J., Li, L., & Turner, J. E. (1989) Exp. Eye Res. 48, 841–854.
27. Rakoczy, P. E., Humphrey, M. F., Cavaney, D. M., Chu, Y., & Constable, I. J. (1993) Invest. Ophthalmol. Vis. Sci. 34, 1845–1852.
28. Prats, H., Kaghad, M., Prats, A. C., Klagsbrun, M., Lelias, J. M., Liauzun, P., Chalon, P., Tauber, J. P., Amalric, F., Smith, J. A., & Caput, D. (1989) Proc. Natl. Acad. Sci. USA 86, 1836–1840.
29. Klagsbrun, M., Smith, S., Sullivan, R., Shing, T., Davidson, S., Smith, J. A., & Sasse, J. (1987) Proc. Natl. Acad. Sci. USA 84, 1839–1843.
30. Renko, N., Quarto, N., Morimoto, T., & Rifkin, D. B. (1990) J. Cell Biol. 109, 1–6.
31. Mignafti, P., Morimoto, T., & Rifkin, D. B. (1992) J. Cell. Physiol. 151, 81–93.
32. Fernig, D. G. & Gallagher, J. T. (1994) Prog. Growth Factor Res. 5, 353–377.
33. Faktorovich, E. G., Steinberg, R. H., Yasumura, D., Matthes, M. T., & LaVail, M. M. (1990) Nature 347, 83–86.
34. Darquy, S. & Reach, G. (1985) Diabetologia 10, 776–780.
35. Chang, P. L., Shen, N., & Westcott, A. (1993) Hum. Gene Ther. 4, 433–440.
36. Deglon, N., Heyd, B., Tan, S. A., Joseph, J. M., Zurn, A. D., & Aebischer, P. (1996) Hum. Gene Ther. 7, 2135–2146.
37. Roberts, T., De Boni, U., & Sefton, M. V. (1996) Biomaterials 17, 267–275.
38. Thu, B., Bruheim, P., Espevik, T., Smidsrod, O., Soon-Shiong, P., & Skjak-Braek, G. (1996a) Biomaterials 17, 1031–1040.
39. Thu, B., Bruheim, P., Espevik, T., Smidsrod, O., Soon-Shiong, P., & Skjak-Braek, G. (1996b) Biomaterials 17, 1069–1079.
40. Honiger, J., Balladur, P., Mariani, P., Calmus, Y., Vaubourdolle, M., Delelo, R., Capeau, J., & Nordlinger, B. (1995) Biomaterials 16, 753–759.
41. Kessler, L., Aprahamian, M., Keipes, M., Damge, C., Pinget, M., & Poinsot, D. (1992) Biomaterials 13, 40–49.
42. Balladur, P., Crema, E., Honiger, J., Calmus, Y., Baudrimont, M., Delelo, R., Capeau, J., & Nordlinger, B. (1995) Surgery 117, 189–194.
43. Maret, A., Galy, B., Amaud, E., Bayard, F., & Prats, H. (1995) Cancer Res. 55, 5075–5079.
44. Huez, I., Créancier, L., Audigier, S., Gensac, M. C., Prats, A. C., & Prats, H. (1998) Mol. Cell. Biol. 18, 6178–6190.

45. Arnaud, E., Touriol, C., Boutonnet, C., Gensac, M. C., Vagner, S., Prats, H., & Prats, A. C. (1999) Mol. Cell. Biol. 19, 505–514.
46. Chow, R. L., Roux, G. D., Roghani, M., Palmer, M. A., Rifkin, D. B., Moscatelli, D. A., & Lang, R. (1995) Development 121, 4383–4393.
47. Bugra, K. & Hicks, D. (1997) J. Mol. Neurosci. 9, 13–25.
48. Cao, W., Wen, R., Li, F., Cheng, T., & Steinberg, R. H. (1997) Ophthalmol. Vis. Sci. 38, 1358–1365.
49. Goureau, O., Lepoivre, M., Becquet, F., & Courtois, Y. (1993a) Neuroreport 5, 233–236.
50. Goureau, O., Lepoivre, M., Becquet, F., & Courtois, Y. (1993b) Proc. Natl. Acad. Sci. USA 90, 4276–4280.
51. McLaren, M. J. & Inana, G. (1997) FEBS Lett. 412, 21–29.
52. Rogelj, S., Weinberg, R. A., Fanning, P., & Klagsbrun, M. (1989) J. Cell. Biochem. 39, 13–23.
53. Morris, P. J. (1996) Trends Biotechnol. 14, 163–167.

What we claim is:

1. A composition comprising encapsulated cells which produce an endostatin or a fibroblast growth factor polypeptide, wherein said encapsulated cells are encapsulated with a biocompatible material of polyacrylonitril-methysulfonate.

2. The composition according to claim 1, wherein said biocompatible material forms a biocomparible microcapsule which prevents entry of host immune cells inside said microcapsules and allow release of said endostatin or said fibroblast growth factor outside of the microcapsule.

3. The composition according to claim 2, wherein said biocompatible microcapsule is comprised of pores having an internal diameter below 400 $\mu$m.

4. The composition according to claim 2, wherein said biocompatible microcapsule is comprised of pores having an internal diameter below 300 $\mu$m.

5. The composition according to claim 1, wherein said encapsulated cells are mammalian cells comprising a nucleic acid encoding said endostatin polypeptide or said fibroblast growth factor polypeptide.

6. The composition according to claim 5, wherein said mammalian cells are selected from the group consisting of fibroblasts, muscle cells, hepatocytes, neural cells, kidney cells, and MDCK cells.

7. The composition according to claim 1, wherein said composition comprises $10^4$ encapsulated cells.

8. The composition according to claim 1, wherein said composition comprises $10^5$ encapsulated cells.

* * * * *

UNITED STATES PATENT AND TRADEMARK OFFICE
CERTIFICATE OF CORRECTION

PATENT NO. : 6,663,894 B2
DATED : December 16, 2003
INVENTOR(S) : Abitbol et al.

It is certified that error appears in the above-identified patent and that said Letters Patent is hereby corrected as shown below:

Title page,
Item [75], Inventors, "Vitlejuif" should read -- Villejuif --

Column 9,
Line 47, "n $\propto$" should read -- n=4 --
Line 48, "P-16" should read -- P16 --

Column 15,
Line 60, "dearly" should read -- clearly --

Column 21,
Line 29, "biocomparible" should read -- biocompatible --

Signed and Sealed this

Fifteenth Day of June, 2004

JON W. DUDAS
*Acting Director of the United States Patent and Trademark Office*

SEQUENCE LISTING

<160> NUMBER OF SEQ ID NOS: 5

<210> SEQ ID NO 1
<211> LENGTH: 206
<212> TYPE: DNA
<213> ORGANISM: Rattus rattus

<400> SEQUENCE: 1

```
cccgggcctc gggccgggga ggaagagtag ctcgccgagg cgccgaggag agcgggccgc      60
cccacagccc gagccggaga gggagcgcga gccgcgccgg ccccggtcgg gcctccgaaa     120
ccatgaactt tctgctgtct tgggtgcatt ggagccttgc cttgctgctc tacctccacc     180
atgccaagtg gtcccaggct gcaccc                                         206
```

<210> SEQ ID NO 2
<211> LENGTH: 79
<212> TYPE: DNA
<213> ORGANISM: Rattus rattus

<400> SEQUENCE: 2

```
atgacttacc catacgatgt tccagattac gctagcttgg gtggtcatat ggccatggag      60
gccccgggga tccgaattc                                                   79
```

<210> SEQ ID NO 3
<211> LENGTH: 558
<212> TYPE: DNA
<213> ORGANISM: Rattus rattus

<400> SEQUENCE: 3

```
gctcatactc atcaggactt tcagccagtg ctccacctgg tggcactgaa cacccccctg      60
tctggaggca tgcgtggtat ccgtggagca gatttccagt gcttccagca agcccgagcc     120
gtggggctgt cgggcacctt ccgggctttc ctgtcctcta ggctgcagga tctctatagc     180
atcgtgcgcc gtgctgaccg ggggtctgtg cccatcgtca acctgaagga cgaggtgcta     240
tctcccagct gggactccct gttttctggc tcccagggtc aactgcaacc cggggcccgc     300
atcttttctt ttgacggcag agatgtcctg agacacccag cctggccgca gaagagcgta     360
tggcacggct cggacccag tgggcggagg ctgatggaga gttactgtga gacatggcga     420
actgaaacta ctggggctac aggtcaggcc tcctccctgc tgtcaggcag gctcctggaa     480
cagaaagctg cgagctgcca caacagctac atcgtcctgt gcattgagaa tagcttcatg     540
acctctttct ccaaatag                                                   558
```

<210> SEQ ID NO 4
<211> LENGTH: 37
<212> TYPE: DNA
<213> ORGANISM: Artificial Sequence

```
<220> FEATURE:
<223> OTHER INFORMATION: PCR Primer

<400> SEQUENCE: 4
ccgactttca ggactactca tacttaaggg taccaaa                              37

<210> SEQ ID NO 5
<211> LENGTH: 67
<212> TYPE: DNA
<213> ORGANISM: Artificial Sequence
<220> FEATURE:
<223> OTHER INFORMATION: PCR Primer

<400> SEQUENCE: 5
gtactggaga aagaggtttc ggccgtctcc tagcgtagtg gtagtggtag tgcacatcgg     60
cgccaaa                                                              67
```